(12) United States Patent
Dervieux

(10) Patent No.: US 9,261,509 B2
(45) Date of Patent: Feb. 16, 2016

(54) METHODS FOR MONITORING METHOTREXATE THERAPY

(75) Inventor: Thierry Dervieux, Irvine, CA (US)

(73) Assignee: Thierry Dervieux, Vista, CA (US)

( * ) Notice: Subject to any disclaimer, the term of this patent is extended or adjusted under 35 U.S.C. 154(b) by 443 days.

(21) Appl. No.: 13/810,683

(22) PCT Filed: Sep. 13, 2011

(86) PCT No.: PCT/US2011/051310
§ 371 (c)(1),
(2), (4) Date: May 20, 2013

(87) PCT Pub. No.: WO2012/037068
PCT Pub. Date: Mar. 22, 2012

(65) Prior Publication Data
US 2013/0230865 A1 Sep. 5, 2013

Related U.S. Application Data

(60) Provisional application No. 61/382,148, filed on Sep. 13, 2010.

(51) Int. Cl.
G01N 33/68 (2006.01)
C12Q 1/68 (2006.01)
G01N 33/573 (2006.01)
G01N 33/50 (2006.01)

(52) U.S. Cl.
CPC ............. *G01N 33/68* (2013.01); *C12Q 1/6883* (2013.01); *G01N 33/50* (2013.01); *G01N 33/573* (2013.01); *C12Q 2600/136* (2013.01); *C12Q 2600/142* (2013.01); *C12Q 2600/158* (2013.01); *G01N 2333/90666* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,582,282 B2 | 9/2009 | Dervieux | |
| 7,695,908 B2 | 4/2010 | Dervieux | |
| 2004/0043441 A1* | 3/2004 | Dervieux | A61K 35/18 435/18 |
| 2007/0093497 A1 | 4/2007 | Walsh | |
| 2010/0159493 A1 | 6/2010 | Dervieux | |
| 2010/0203507 A1 | 8/2010 | Dervieux | |
| 2010/0203508 A1* | 8/2010 | Dervieux | C12Q 1/6883 435/6.13 |
| 2010/0203539 A1* | 8/2010 | Dervieux | C12Q 1/6883 435/6.18 |
| 2013/0131072 A1* | 5/2013 | Dervieux | C12Q 1/6883 514/249 |

FOREIGN PATENT DOCUMENTS

| | | |
|---|---|---|
| WO | 2005/022118 WO | 3/2005 |
| WO | 2006/116684 WO | 11/2006 |

OTHER PUBLICATIONS

Ermens A. et al. Effect of Nitrous Oxide and MTX on Folate Coenzyme Pools of Blast Cells from Leukemia Patients. Leukemia Research 15(2/3)165-171, 1991.*
Ranganathan P. An Update on Methotrexate Pharmacogenetics in RA. Pharmacogenetics 9(4)439-451, 2008.*
Allegra CJ, Drake J C, Jolivet J and Chabner B A (1985) Inhibition of Phosphoribosylaminoimidazolecarboxamide Transformylase by Methotrexate and Dihydrofolic Acid Polyglutamates. Proc Natl Acad Sci U S A 82:4881-4885.
Allegra CJ, Fine R L, Drake J C and Chabner B A (1986) The Effect of Methotrexate on Intracellular Folate Pools in Human MCF-7 Breast Cancer Cells. Evidence for Direct Inhibition of Purine Synthesis. J Biol Chem 261:6478-6485.
Allegra CJ, Hoang K, Yeh G C, Drake J C and Baram J (1987) Evidence for Direct Inhibition of De Novo Purine Synthesis in Human MCF-7 Breast Cells As a Principal Mode of Metabolic Inhibition by Methotrexate. J Biol Chem 262:13520-13526.
Angelis-Stoforidis P, Vajda F J and Christophidis N (1999) Methotrexate Polyglutamate Levels in Circulating Erythrocytes and Polymorphs Correlate With Clinical Efficacy in Rheumatoid Arthritis. Clin Exp Rheumatol JID—8308521 17:313-320.
Bagley PJ and Selhub J (1998) A Common Mutation in the Methylenetetrahydrofolate Reductase Gene Is Associated With an Accumulation of Formylated Tetrahydrofolates in Red Blood Cells. Proceedings of the National Academy of Sciences of the United States of America 95:13217-13220.
Chabner BA, Allegra C J, Curt G A, Clendeninn N J, Baram J, Koizumi S, Drake J C and Jolivet J (1985) Polyglutamation of Methotrexate. Is Methotrexate a Prodrug? J Clin Invest 76:907-912.
Chladek J, Martinkova J, Simkova M, Vaneckova J, Koudelkova V and Nozickova M (1998) Pharmacokinetics of Low Doses of Methotrexate in Patients With Psoriasis Over the Early Period of Treatment. Eur J Clin Pharmacol 53:437-444.
Covey, et al. (1980) "Polyglutamate derivativies of folic acid coenzymes and methotrexate," Life Sciences, 26 (9):665-678.
Cronstein BN (2005) Low-Dose Methotrexate: a Mainstay in the Treatment of Rheumatoid Arthritis. Pharmacol Rev 57:163-172.
Cronstein BN, Naime D and Ostad E (1993) The Antiinflammatory Mechanism of Methotrexate. Increased Adenosine Release at Inflamed Sites Diminishes Leukocyte Accumulation in an in Vivo Model of Inflammation. J Clin Invest JID—7802877 92:2675-2682.
Dalrymple JM, Stamp L K, O'Donnell J L, Chapman P T, Zhang M and Barclay M L (2008) Pharmacokinetics of Oral Methotrexate in Patients With Rheumatoid Arthritis. Arthritis Rheum 58:3299-3308.

(Continued)

*Primary Examiner* — Ralph Gitomer
(74) *Attorney, Agent, or Firm* — McDonnell Boehnen Hulbert & Berghoff LLP

(57) ABSTRACT

The present invention provides methods for assessing efficacy of a methotrexate (MTX) dosing regimen in a patient.

22 Claims, 3 Drawing Sheets

(56) References Cited

OTHER PUBLICATIONS

Dervieux T, Zablocki R, and Kremer, Joel M. The Sequential Addition of Glutamic Residues on Methotrexate Selectively Potentiates the Efficacy of This Prodrug in Rheumatoid Arthritis [abstract]. Arthritis Rheum 59, S399. 2009b.

Dervieux T, Zablocki R and Kremer J M (2009a) Preliminary Estimates and Significance of Red Blood Cell Methotrexate Polyglutamate Measurements in the Rheumatology Practice Setting. Arthritis and Rheumatism 60: Abstract 1619.

Dervieux T, Furst D, Lein D O, Capps R, Smith K, Caldwell J and Kremer J (2005) Pharmacogenetic and Metabolite Measurements Are Associated With Clinical Status in Patients With Rheumatoid Arthritis Treated With Methotrexate: Results of a Multicentred Cross Sectional Observational Study. Ann Rheum Dis 64:1180-1185.

Dervieux T, Furst D, Lein D O, Capps R, Smith K, Walsh M and Kremer J (2004) Polyglutamation of Methotrexate With Common Polymorphisms in Reduced Folate Carrier, Aminoimidazole Carboxamide Ribonucleotide Transformylase, and Thymidylate Synthase Are Associated With Methotrexate Effects in Rheumatoid Arthritis. Arthritis Rheum JID—0370605 50:2766-2774.

Dervieux T, Greenstein N and Kremer J (2006) Pharmacogenomic and Metabolic Biomarkers in the Folate Pathway and Their Association With Methotrexate Effects During Dosage Escalation in Rheumatoid Arthritis. Arthritis Rheum 54:3095-3103.

Ercikan-Abali EA, Banerjee D, Waltham M C, Skacel N, Scotto K W and Bertino J R (1997) Dihydrofolate Reductase Protein Inhibits Its Own Translation by Binding to Dihydrofolate Reductase MRNA Sequences Within the Coding RegionGCá. Biochemistry 36:12317-12322.

Ermens, et al., (1991) "Effect of nitrous oxide and methotrexate on folate coenzyme pools of blast cells from leukemia patients," Leukemia Research, 15(2-3): 165-171.

Fazili Z, Pfeiffer C M, Zhang M, Jain R B and Koontz D (2008) Influence of 5,10-Methylenetetrahydrofolate Reductase Polymorphism on Whole-Blood Folate Concentrations Measured by LC-MS/MS, Microbiologic Assay, and Bio-Rad Radioassay. Clinical Chemistry 54:197-201.

Garratt LC, Ortori C A, Tucker G A, Sablitzky F, Bennett M J and Barrett D A (2005) Comprehensive Metabolic Profiling of Mono- and Polyglutamated Folates and Their Precursors in Plant and Animal Tissue Using Liquid Chromatography/Negative Ion Electrospray Ionisation Tandem Mass Spectrometry. Rapid Commun Mass Spectrom 19:2390-2398.

Hornung N, Ellingsen T, Attermann J, Stengaard-Pedersen K and Poulsen J H (2008) Patients With Rheumatoid Arthritis Treated With Methotrexate (MTX): Concentrations of Steady-State Erythrocyte MTX Correlate to Plasma Concentrations and Clinical Efficacy. J Rheumatol 35:1709-1715.

Kremer JM and Lee J K (1986) The Safety and Efficacy of the Use of Methotrexate in Long-Term Therapy for Rheumatoid Arthritis. Arthritis Rheum JID—0370605 29:822-831.

Matthews RG and Daubner S C (1982) Modulation of Methylenetetrahydrofolate Reductase Activity by S-Adenosylmethionine and by Dihydrofolate and Its Polyglutamate Analogues. Adv Enzyme Regul 20:123-131.

Pfeiffer, et al. (2004) "Determination of folate vitamers in human serum by stable-isotope-dilution tandem mass spectrometry and comparison with radioassay and microbiologic assay," Clinical Chemistry, 50(2):423-432, 2004.

Smulders YM, Smith D E, Kok R M, Teerlink T, Gellekink H, Vaes W H, Stehouwer C D and Jakobs C (2007) Red Blood Cell Folate Vitamer Distribution in Healthy Subjects Is Determined by the Methylenetetrahydrofolate Reductase C677T Polymorphism and by the Total Folate Status. J Nutr Biochem 18:693-699.

Stamp LK, Chapman P T, O'Donnell J L, Zhang M, James J, Frampton C, Barclay M L, Kennedy M A and Roberts R L (2010a) Polymorphisms Within the Folate Pathway Predict Folate Concentrations but Are Not Associated With Disease Activity in Rheumatoid Arthritis Patients on Methotrexate. Pharmacogenet Genomics 20:367-376.

Stamp LK, O'Donnell J L, Chapman P T, Zhang M, James J, Frampton C and Barclay M L (2010b) Methotrexate Polyglutamate Concentrations Are Not Associated With Disease Control in Rheumatoid Arthritis Patients Receiving Long-Term Methotrexate Therapy. Arthritis Rheum 62:359-368.

International Search Report PCT/US2011/051310, mailed Dec. 27, 2011.

* cited by examiner

Figure 1A-C

Figure 3A
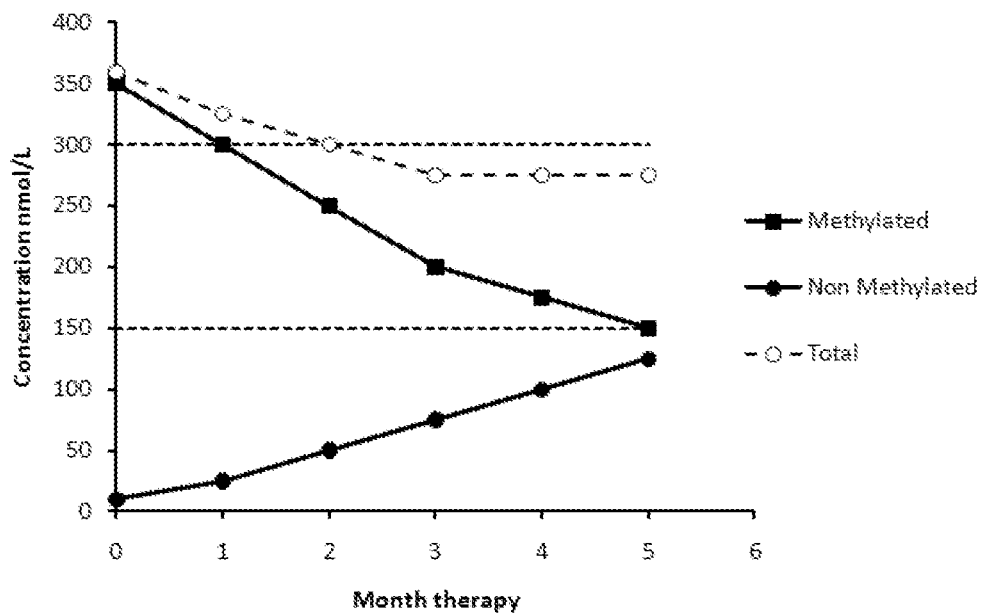
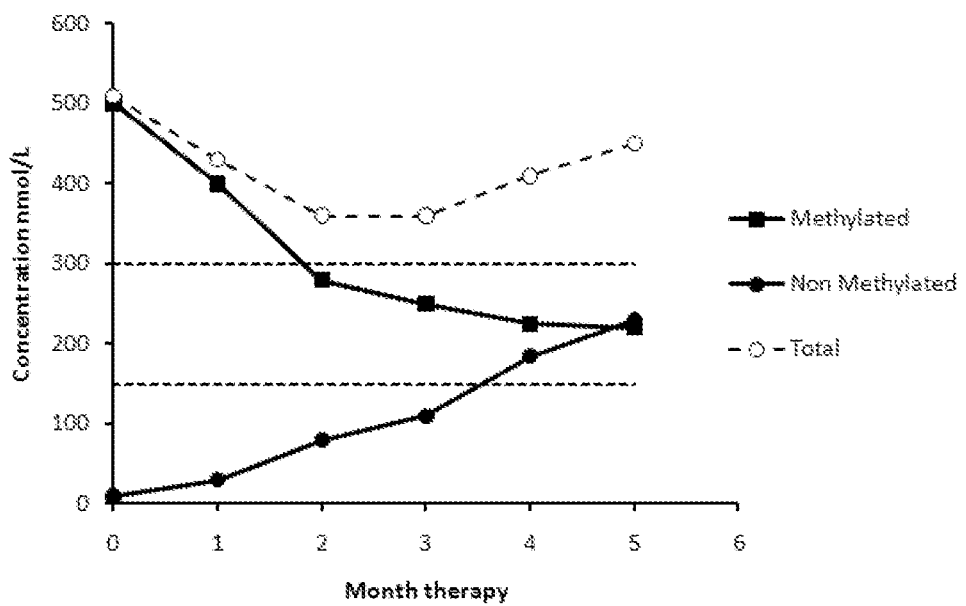
Figure 3B

SEQUENCE LISTING

<160> NUMBER OF SEQ ID NOS: 1

<210> SEQ ID NO 1
<211> LENGTH: 187
<212> TYPE: PRT
<213> ORGANISM: Homo sapiens

<400> SEQUENCE: 1

```
Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
                20                  25                  30

Arg Tyr Phe Gln Arg Met Thr Thr Thr Ser Ser Val Glu Gly Lys Gln
            35                  40                  45

Asn Leu Val Ile Met Gly Lys Lys Thr Trp Phe Ser Ile Pro Glu Lys
        50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
                100                 105                 110

Val Trp Ile Val Gly Gly Ser Ser Val Tyr Lys Glu Ala Met Asn His
            115                 120                 125

Pro Gly His Leu Lys Leu Phe Val Thr Arg Ile Met Gln Asp Phe Glu
        130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
                180                 185
```

METHODS FOR MONITORING METHOTREXATE THERAPY

CROSS REFERENCE

This application claims priority to U.S. Provisional Patent Application Ser. No. 61/382,148 filed Sep. 13, 2010, incorporated by reference herein in its entirety.

BACKGROUND

Methotrexate (MTX) forms the cornerstone treatment of various autoimmune disorders including rheumatoid arthritis (RA), a debilitating disease affecting approximately 1% of the population. The cessation of purine, pyrimidine and protein synthesis following MTX is believed to produce anti-inflammatory effects through an activation of this prodrug into methotrexate polyglutamates (Dervieux et al., 2004). More precisely, these polyglutamated metabolites are retained intracellularly and inhibit de novo purine biosynthesis (i.e. AICAR transformylase) to release adenosine, a potent anti-inflammatory agent (Cronstein, 2005). Data indicate that the selective addition of glutamic residues onto MTX significantly potentiate the efficacy of this prodrug in vitro (Allegra et al., 1985) with the pentaglutamylated form of MTX being 2500-hundred fold more potent than MTX itself against AICAR transformylase (Allegra et al., 1987). Moreover, the notion that MTX's effects are produced by long chain MTX-PGs versus short chains MTXPGs is supported by the observation that the number of glutamic residues on MTX is associated with the clinical effects of this prodrug in rheumatoid arthritis (Dervieux T et al., 2009b). Several clinical applications have been derived from the observations that MTXPGs are associated with the anti-inflammatory effects of MTX (Angelis-Stoforidis et al., 1999; Dervieux et al., 2004; Dervieux et al., 2005; Hornung et al., 2008), and the drug monitoring of low dose MTX therapy using the surrogate red blood cells can be helpful to assess exposure, compliance, and thus establish whether an appropriate dose of MTX is being administered to any given patients. (Dervieux T et al., 2009a). In particular, it is well recognized that approximately 5-10% of individuals do not metabolize MTX effectively, with virtually the totality of the drug excreted unchanged in the urine within the first few hours following the once weekly administration of the drug (Chladek et al., 1998).

However, under its current format there are several drawbacks with the usage of RBC MTXPGs in clinical practice. First, steady state concentrations of long chain MTXPGs in erythrocytes are only achieved after several months of therapy (Dalrymple et al., 2008) and while useful to address potential pharmacokinetics issues (e.g. rapid excretion phenotype described above), MTXPGs are not ideal pharmacodynamic markers indicating whether control of disease activity is achieved in any given patients. RBC MTXPGs have also poor predictive value before 3-4 months therapy which limit their utility, particularly given that significant clinical benefit from MTX in RA is usually observed in the first 6 weeks of therapy, at a time where very polyglutamation is detectable in erythrocytes (Kremer and Lee, 1986).

It follows that novel markers of MTX effects and exposure complementing MTXPGs measurements in the surrogate erythrocyte or target lymphocyte could be extremely useful to improve the performances of the drug monitoring assay of MTX therapy in patients suffering from cancer, inflammatory disease, and autoimmune disorders. Such method would be particularly useful early in the course of MTX treatment (1-4 weeks therapy) and provide a valuable tool to identify patients presenting defective MTX metabolism such as those with the rapid excretory phenotype (and hence no formation of MTXPGs). Currently, no method is available to directly or indirectly quantify MTXPGs early in course of MTX therapy (i.e, one week), or after a single dose of MTX, owing to the low concentrations of these metabolites in targets cells and the inherent sensitivity challenges associated with their detection.

SUMMARY OF THE INVENTION

In a first aspect, the present invention provides methods for assessing efficacy of an anti-folate dosing regimen in a patient, comprising
  (a) determining a post-treatment amount of dihydrofolate reductase (DHFR) in a biological sample from the patient after initiation or modification of anti-folate treatment in the patient;
  (b) comparing the amount of DHFR to a patient pre-treatment or pre-modification DHFR standard to determine a level of DHFR induction; and
  (c) assessing efficacy of the anti-folate dosing regimen in the patient based on the level of DHFR induction.

In a second aspect, the present invention provides methods for assessing efficacy of an anti-folate dosing regimen in a patient, comprising
  (a) determining an intracellular amount of
    (i) 5-methyltetrahydrofolate (5CH3THF) polyglutamates (PGs); and
    (ii) non-methylated folate PGs
  in a biological sample from the patient before or after initiation of anti-folate treatment or modification of anti-folate treatment in the patient; and
  (b) assessing efficacy of the anti-folate dosing regimen in the patient based on the amount of 5CH3THF PGs and/or the amount of non-methylated folate PGs.

In a third aspect, the present invention provides non-transitory computer readable storage media, for automatically carrying out the methods of the invention, or certain steps thereof (ex: determining, comparing, and/or assessing steps), on a detection device

DESCRIPTION OF THE FIGURES

FIG. 3 shows an exemplary change in whole blood methylated and non-methylated folate concentrations in an RA patient undergoing MTX therapy.

DETAILED DESCRIPTION OF THE INVENTION

Figure 1:
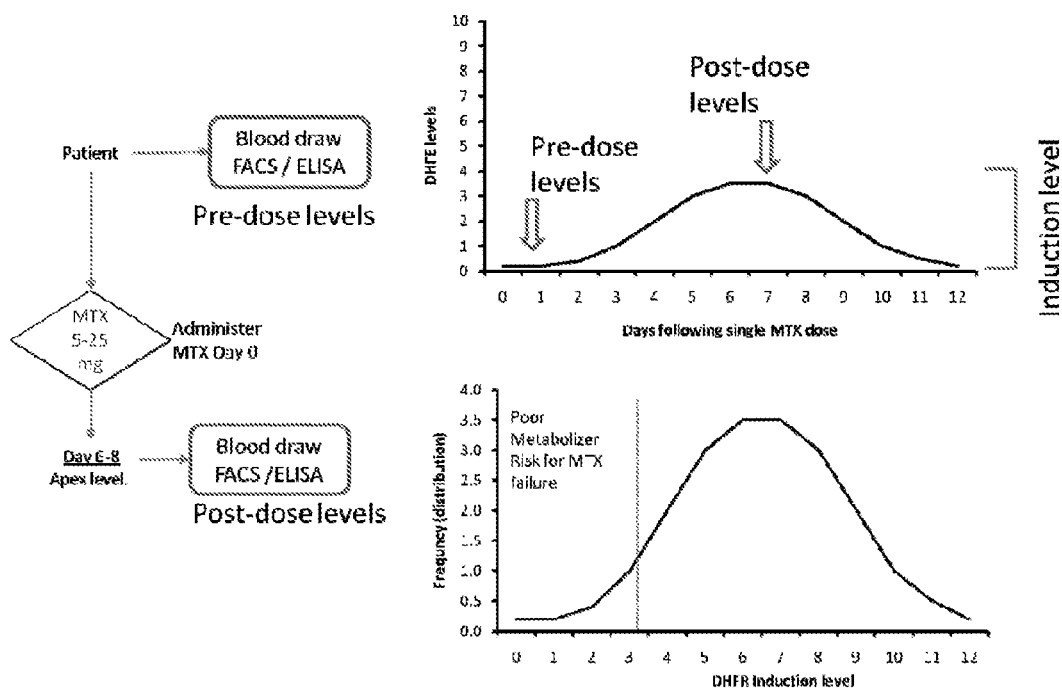
FIG. 1 (A-C) provide an exemplary flowchart of the methods of the invention, and exemplary graphs showing DHFR induction levels after methotrexate administration.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic*

*Technique*, 2<sup>nd</sup> Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods for assessing efficacy of a anti-folate dosing regimen in a patient, comprising:

(a) determining a post-treatment amount of dihydrofolate reductase (DHFR) in a biological sample from the patient after initiation or modification of anti-folate treatment in the patient;

(b) comparing the amount of DHFR to a patient pre-treatment or pre-modification DHFR standard to determine a level of DHFR induction; and (c) assessing efficacy of the anti-folate dosing regimen in the patient based on the level of DHFR induction.

Any suitable anti-folate may be used in the methods of the invention, including but not limited to methotrexate (MTX), trimethoprim, pyrimethamine, pemetrexed, aminopterin, raltitrexed, and CH1054. In a preferred embodiment, the antifolate is methotrexate (MTX). It will be understood that, while further embodiments focus on methotrexate as the antifolate, that any other anti-folate may be substituted for methotrexate in discussions of these embodiments, unless the context clearly dictates otherwise.

In one preferred embodiment, the methods of this aspect of the invention provide novel markers of MTX effects and exposure at early time points, as early as 6 days after MTX treatment and after administration of a single MTX dose. As such, the methods of the invention are valuable for improving the performances of MTX therapy monitoring assays in patients suffering from cancer, inflammatory disease, and autoimmune disorders. Currently, no method is available to directly or indirectly quantify MTXPGs early in course of MTX therapy (i.e, one week), or after a single dose of MTX, owing to the low concentrations of these MTXPGs in targets cells and the inherent sensitivity challenges associated with their detection. The present invention addresses these limitations.

While not being bound by any mechanism of action, the methods involve indirectly measuring MTXPG levels, and thus increased efficacy, by detecting DHFR levels, as DHFR protein levels rapidly increase upon exposure to MTX. This is an unexpected finding, given the knowledge in the art that MTX in an inhibitor of DHFR and that an increase in DHFR activity (amplification) is associated with MTX resistance.

Methotrexate (MTX) is well known in the art as an inhibitor of purine and thymidine synthesis and amino acid interconversion. MTX also exhibits anti-proliferative activity through inhibition of thymidylate synthesis, which is required to synthesize DNA. MTX, its synthesis, and its properties are described in further detail in U.S. Pat. Nos. 2,512, 572; 3,892,801; 3,989,703; 4,057,548; 4,067,867; 4,079,056; 4,080,325; 4,136,101; 4,224,446; 4,306,064; 4,374,987; 4,421,913; and 4,767,859. Methods for using MTX to treat cancer are described, for example, in U.S. Pat. Nos. 4,106, 488; 4,558,690; and 4,662,359. MTX is known to be useful in the treatment of a variety of inflammatory diseases, autoimmune diseases, and cancers.

The methods of the invention can be used in combination with MTX administered at any dose determined suitable for a given patient by an attending physician. In one embodiment, the methods are used in conjunction with low dose MTX therapy. As used herein, the term "low dose MTX therapy" refers to administration of MTX to a subject at a dose that is less than about 40 mg/m$^2$ of body surface per week. Typically, low dose MTX therapy is administered orally at a dose in the range of from about 2.5 mg/m$^2$ to about 40 mg/m$^2$ of body surface per week, for example, from about 2.5 mg/m$^2$ to about 25 mg/m$^2$ of body surface per week, depending upon the condition being treated. In another embodiment, the methods are used in conjunction with high dose MTX therapy. The term "high dose MTX therapy" as used herein refers to administration of MTX to a subject at a dose that is at least about 100 mg/m$^2$ of body surface per day, for example, at least about 100, 250, 500, 750, 1000, 1500, 3000, or 5000 mg/m$^2$ of body surface per day. One skilled in the art understands that a high dose MTX therapy is frequently used as an anti-cancer therapeutic and can be administered at doses up to about 5 g/m$^2$ of body surface per day or higher depending upon the condition or disease being treated. One skilled in the art recognizes that the doses of MTX typically used in high dose MTX therapy can be administered, for example, intravenously or orally and that such high dose MTX therapy generally requires a period of recovery, which can include leucovorin rescue or another form of folate replacement. In another embodiment, the methods are used in conjunction with intermediate dose MTX therapy. The term "intermediate dose MTX therapy" refers to administration of MTX to a subject at a dose that is typically between a low dose and a high dose of MTX, for example, between about 100 mg/m$^2$ of body surface per week to about 250 mg/m$^2$ of body surface per day.

It will be understood that the dosage ranges of MTX set forth above in the definitions of low, intermediate, and high dose MTX therapy are generalized with respect to treatment of a variety of diseases and that the range of MTX dose that is administered for one disease can differ from the range administered for another. Accordingly, a dose of at least about 40 mg/m$^2$ of body surface per day, although generally considered high dose MTX therapy, may be considered by those skilled in the art of cancer therapy as a relatively low dose for treating cancer. Similarly, a dose of about 30 mg/m$^2$ of body surface per week, although generally considered as low dose MTX therapy, may be considered by those skilled in the art of rheumatology as a relatively high dose for treating rheumatoid arthritis.

The patient can be any suitable patient, preferably a human patient, in need of MTX therapy. In one preferred embodiment, the patient suffers from an inflammatory disease or cancer. The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease, rheumatoid diseases (e.g., rheumatoid arthritis), other arthritic diseases (e.g., acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, venereal arthritis, viral arthritis), fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis. Inflammatory bowel diseases are chronic inflammatory diseases of the gastrointestinal tract which include, without limitation, Crohn's disease, ulcerative colitis, and indeterminate colitis. Rheumatoid arthritis is a chronic inflammatory disease primarily of the joints, usually polyarticular, marked by inflammatory changes in the synovial membranes and articular structures and by muscle atrophy and rarefaction of the bones.

The term "cancer" refers to any of various malignant neoplasms characterized by the proliferation of anaplastic cells that tend to invade surrounding tissue and metastasize to new body sites. Examples of different types of cancer include, but are not limited to, lung cancer, breast cancer, bladder cancer, thyroid cancer, liver cancer, pleural cancer, pancreatic cancer, ovarian cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, blood cancers, osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia.

In another preferred embodiment, the patient suffers from an autoimmune disorder. The term "autoimmune disease" refers to a disease or disorder resulting from an immune response against a self-tissue or tissue component and includes a self-antibody response or cell-mediated response. The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjogren's syndrome, and multiple sclerosis. In a preferred embodiment, the autoimmune disorder is selected from the group consisting of rheumatoid arthritis, Crohn's disease, ulcerative colitis, and systemic lupus erythematosus.

The MTX therapy may involve comprise any suitable route of MTX administration, including oral administration, administration as a suppository, topical contact, parenteral (ex: intravenous, intramuscular, intra-arteriole, intradermal, subcutaneous, intraperitoneal, intraventricular, and intracranial, etc.), intranasal or subcutaneous administration, the implantation of a slow-release device, e.g., a mini-osmotic pump, to the patient, transmucosal (e.g., buccal, sublingual, palatal, gingival, nasal, vaginal, rectal, or transdermal), the use of liposomal formulations, intravenous infusion, transdermal patches, etc.

The amino acid sequence of human DHFR is shown below. As will be appreciated by those of skill in the art, individual patients may have slightly modified DHFR protein sequences, and thus the methods of the invention are not limited to determining the level of DHFR as defined by the specific amino acid sequence of SEQ ID NO:1.

Any suitable technique can be used for determining the amount of DHFR in the biological sample, including but not limited to enzyme linked immunoabsorbant assays (ELISA), mass spectrometry, dipstick assays, flow cytometry, absorption spectroscopy, fluorescence-activated cell sorting (FACS), Western blotting, reverse-transcription-PCR analysis, etc. Antibodies selective for DHFR are commercially available (for example, from Abcam, Santa Cruz Biotechnologies, Sigma, etc.).

Any suitable biological sample from the patient can be used, including but not limited to whole blood, erythrocytes, reticulocytes, leukocytes, peripheral mononuclear cells, CD4+ cells, CD8+ cells, monocytes, neutrophils, and platelets. In a preferred embodiment, the biological sample comprises erythrocytes, leukocytes, and/or peripheral mononuclear cells. In one preferred embodiment, As used herein, "initiation of treatment" means the first administration of MTX therapy in patient who had not been receiving MTX therapy (ex: MTX-naïve patient; patient who received MTX therapy in the past, but had not been taking MTX prior to reintroduction of therapy). As used herein, "modification of treatment" means any change in the MTX therapy, including but not limited to (a) an increase in MTX dosage; (b) a decrease in MTX dosage; and (c) a change in route of MTX administration (ex: switch from oral to parenteral administration; switch from parenteral to oral administration).

In one preferred embodiment, the determining comprises determining a post-treatment amount of DHFR in the biological sample from the patient after initiation of MTX treatment in the patient. In another preferred embodiment, the determining comprises determining a post-treatment amount of DHFR in the biological sample from the patient after modification of MTX treatment in the patient.

The methods comprise comparing the amount of DHFR to a patient pre-treatment or pre-modification DHFR standard to determine a level of DHFR induction. As used herein, "pre-treatment or pre-modification DHFR standard" means a baseline sample from the patient, where the sample is obtained either prior to initiation of MTX therapy, or prior to a change in MTX therapy (ie: prior to increasing dosage, decreasing dosage, changing route of administration, etc.). The "pre-treatment" and "post-treatment" DHFR levels are compared to determine a level of MTX-mediate DHFR induction in the patient. The level of DHR induction can be determined at any suitable time point after initiation or modification of MTX therapy. In one preferred embodiment, the level of DHFR induction is determined between about 6 days and about 3 months after initiation or modification of MTX therapy. In further preferred embodiments, the DHFR induction is determined between about 6 days and about 2 months; between about 6 days and about 1 month; between about 6 days and about 20 days; between about 6 days and about 15 days; between about 6 days and about 10 days; or between about 6 days and about 8 days after initiation or modification of MTX therapy. In another preferred embodiment, the biological sample comprises erythrocytes and the DHFR induction is determined between about 1 month and about 2 months after initiation or modification of MTX therapy. In a further preferred embodiment, the biological sample comprises leukocytes, and the level of DHFR induction is determined between about 6 days and about 8 days after initiation or modification of MTX therapy.

In a preferred embodiment that can be combined with any embodiment herein, the patient is administered a single MTX dose prior to determining the post-treatment or post-modification amount of DHFR in the biological sample. In a preferred embodiment, this embodiment is combined with the embodiment wherein the biological sample comprises leukocytes, and the level of DHFR induction is determined between about 6 days and about 8 days after initiation or modification of MTX therapy. In another preferred embodiment, this embodiment is combined with the embodiment wherein the biological sample comprises erythrocytes and the DHFR induction is determined between about 1 month and about 2 months after initiation or modification of MTX therapy.

In another embodiment that can be combined with any of the embodiments herein, the methods of this aspect of the invention further comprise comparing the level of DHFR induction to control, and assessing efficacy of the MTX dosing regimen in the patient based on the comparison of the level of DHFR induction to control. In this embodiment, the level of induction in the patient is compared to any suitable external control (ie: a control not directly obtained from the patient being treated) to provide the assessment of MTX efficacy. The control may be any suitable control, including but not limited to previously determined reference standards based on populations of DHFR induction levels in patients receiving MTX therapy.

As used herein, "assessing efficacy of the MTX dosing regimen in the patient" based on the level of DHFR induction, or on the comparison of the DHFR induction level to control, can include any suitable assessment, including an assessing MTX treatment efficacy in the patient, determining an appropriate MTX dosing regimen in the patient, assessing a risk of toxicity to MTX therapy in the patient, assessing a propensity for the patient to retain/rapidly excrete MTX, and assessing patient compliance with a prescribed MTX dosing regimen. In one preferred embodiment, the levels of DHFR induction are determined to assess the efficacy of a prescribed MTX dosing regimen in the patient. The fold induction in DHFR or the absolute level DHFR changes from baseline after a single dose MTX not only indicate whether MTX has been retained in intracellularly, but also indicate quantitatively the extend of the bioactivation of the drug. Thus DHFR levels in the methods of the invention serve as a marker of MTX early exposure at a time where MTXPGs are usually not detected in circulation.

Each of these embodiments described above for determining the level of DHFR induction permit assessment of a prescribed MTX dosing regimen in the patient at a very early stage in treatment, thus permitting rapid identification of issues that should be considered by an attending physician in determining an appropriate MTX dosing regimen in the patient. For example, in one preferred embodiment, a level of DHFR induction less than about 2-fold in the patient (ie: 2 fold increase in DHFR levels in the biological sample after MTX therapy initiation or modification) indicates that the MTX dosage administered to the patient is inadequate to result in a desired clinical outcome. Individuals presenting with low DHFR levels indicate low polyglutamation and retention of MTX. These patients may be underdosed and require intervention consisting of a switch from oral to parenteral MTX or an increase in MTX dose. Thus, in one embodiment, a level of DHR induction below 2 fold would indicate a need to increase MTX dosage administered to the patient. Thus, in various embodiments, a DHFR induction level of below 2-fold, 1.9-fold, 1.8-fold, 1.7-fold, 1.6-fold, 1.5-fold, 1.4-fold, 1.3-fold, 1.2-fold, 1.1-fold, 1.0-fold, 0.9-fold, 0.8-fold, 0.7-fold, 0.6-fold, 0.5-fold, 0.4-fold, 0.3-fold, 0.2-fold, or 0.1-fold would indicate a need to increase MTX dosage administered to the patient, such as indicating that a patient being treated with oral MTX should be switched to parenteral MTX administration. In another embodiment, a level of DHFR induction of at least about 10 fold in a patient being treated with MTX would indicate a likelihood of toxicity in the patient, thus indicating that a lower MTX dosage should be considered or a switch to a therapeutic. Thus, in various embodiments, a DHFR induction level of at least 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, or greater indicate a likelihood of toxicity in the patient, thus indicating that a lower MTX dosage should be considered or a switch to a therapeutic.

In another embodiment, a level of DHFR induction compared to control in the lower $10^{th}$ percentile of induction (preferably the lower $9^{th}$, $8^{th}$, $7^{th}$, $6^{th}$, $5^{th}$, $4^{th}$, $3^{rd}$, $2^{nd}$. or $1^{st}$ percentile of induction) indicates that the patient is a rapid excretor of MTX, since low DHFR induction indicates low systemic MTX exposure (and thus lower efficacy). Approximately 5-10% of individuals do not metabolize MTX effectively, with virtually the totality of the drug excreted unchanged in the urine within the first few hours following the once weekly administration of the drug. Such patients will show a low level of DHFR induction, and thus this embodiment can be used, for example, to indicate patients that might benefit from switching to an alternative drug therapy.

In another embodiment, a level of DHFR induction compared to control in the upper $10^{th}$ percentile of induction (preferably the upper $9^{th}$, $8^{th}$, $7^{th}$, $6^{th}$, $5^{th}$, $4^{th}$, $3^{rd}$, $2^{nd}$, or $1^{st}$ percentile of induction) indicates that the risk of MTX toxicity is increased in the patient. This method can also use to monitor compliance with a prescribed MTX treatment regimen, as the return of DHFR levels to predose levels indicate the absence of MTX in cells, and thus non-compliance with the prescribed treatment regimen.

In a second aspect, the present invention provides methods for assessing efficacy of a anti-folate dosing regimen in a patient, comprising
(a) determining an intracellular amount of
 (i) 5-methyltetrahydrofolate (5CH3THF) polyglutamates (PGs); and
 (ii) non-methylated folate PGs
in a biological sample from the patient before or after initiation of anti-folate treatment or modification of anti-folate treatment in the patient; and
(b) assessing efficacy of the anti-folate dosing regimen in the patient based on the amount of 5CH3THF PGs and/or the amount of non-methylated folate PGs.

Any suitable anti-folate may be used in the methods of the invention, including but not limited to methotrexate (MTX), trimethoprim, pyrimethamine, pemetrexed, aminopterin, raltitrexed, and CH1054. In a preferred embodiment, the anti-folate is methotrexate (MTX). It will be understood that, while further embodiments focus on methotrexate as the anti-folate, that any other anti-folate may be substituted for methotrexate in discussions of these embodiments, unless the context clearly dictates otherwise.

All terms used in the first aspect of the invention carry the same meaning in this second aspect, such as definitions and embodiments of patients, MTX dosing regimens and routes of administration, biological samples, "before or after initiation of MTX treatment or modification of MTX treatment in the patient," etc. Thus, for example, the patient may be one suffering from an inflammatory disease, cancer, or an autoimmune disorder (including but not limited to rheumatoid arthritis, Crohn's disease, ulcerative colitis, and systemic lupus erythematosus). Similarly, any suitable biological sample can be used, including whole blood, erythrocytes, reticulocytes, leukocytes, peripheral mononuclear cells, CD4+ cells, CD8+ cells, monocytes, neutrophils, and platelets. In a preferred embodiment, the biological sample comprises whole blood, leukocytes, and/or erythrocytes.

Similarly, all embodiments and combinations of embodiments of terms from the first aspect of the invention can be used herein.

The present invention provides method for optimizing antifolate therapy by measuring unmethylated and methylated folate polyglutamate concentrations in the biological sample. The methods of this aspect of the invention provide novel markers of MTX effects and exposure at early time points, as early as 6 days after MTX treatment and after administration of a single MTX dose. As such, the methods of the invention are valuable for improving the performances of MTX therapy monitoring assays in patients suffering from cancer, inflammatory disease, and autoimmune disorders. Currently, no method is available to directly or indirectly quantify MTX-PGs early in course of MTX therapy (i.e, one week), or after a single dose of MTX, owing to the low concentrations of these MTXPGs in targets cells and the inherent sensitivity challenges associated with their detection. The present invention addresses these limitations.

As used herein, "intracellular" refers to the fact that PGs are only found intracellularly. Thus, the methods may involve biological sample lysis/extract preparation, while still measuring "intracellular" PG levels.

The level of folate PGs can be determined at any suitable time point after initiation or modification of MTX therapy. In one preferred embodiment, the level of folate PGs is determined between about 6 days and about 3 months after initiation or modification of MTX therapy. In further preferred embodiments, the level of folate PGs is determined between about 6 days and about 2 months; between about 6 days and about 1 month; between about 6 days and about 20 days; between about 6 days and about 15 days; between about 6 days and about 10 days; or between about 6 days and about 8 days after initiation or modification of MTX therapy. In another preferred embodiment, the biological sample comprises erythrocytes or whole blood and the level of folate PGs is determined between about 1 month and about 2 months after initiation or modification of MTX therapy. In a further preferred embodiment, the biological sample comprises leukocytes, and the level of folate PGs is determined between about 6 days and about 8 days after initiation or modification of MTX therapy.

In one preferred embodiment, determining the intracellular amount of 5CH3THF PGs and non-methylated folate PGs is carried out after initiation of MTX treatment in the patient. In another preferred embodiment, determining the intracellular amount of 5CH3THF PGs and non-methylated folate PGs is carried out after modification of MTX treatment in the patient.

In one embodiment, the non-methylated PGs are selected from the group consisting of tetrahydrofolate (THF) PGs; dihydrofolate polyglutamates, 5 methylenetetrahydrofolate (5MeTHF) PGs; 5,10 methylenetetrahydrofolate (5,10CH2THF) PGs; and 10-formyltetrahydrofolate (10CHOTHF) PGs. As will be understood by those of skill in the art, the specific non-methylated PGs measured will be a function of the cell sample used; the methods comprise determining the total amount of intracellular, non-methylated PGs in the biological sample. In a preferred embodiment, the non-methylated PGs are 5,10 methylenetetrahydrofolate (5,10CH2THF), PGs, 10-formyltetrahydrofolate (10CHOTHF) PGs, and dihydrofolate polyglutamates. In this and other embodiments, it is preferred that the biological sample is whole blood, where the all cells in the whole blood sample are lysed and the PGs are converted to MGs by the gamma-glutamyl hydrolase in plasma.

In one embodiment, the methods comprise directly measuring the 5CH3THF PGs and the non-methylated folate PGs using standard techniques, such as those disclosed in, for example, Bagley et al. Clin. Chem 46(3):404-411 (2000). Determining the intracellular amount of 5CH3THF PGs and non-methylated folate PGs may be done by techniques including, but not limited to, reverse phase high performance liquid chromatography combined with tandem mass spectrometric detection (LC MS/MS), a microbiological assay, a dipstick assay, and liquid chromatography coupled with fluorometric detection.

In a preferred embodiment, the biological sample is treated to convert intracellular folate PGs in the biological sample to monoglutamates (MGs) prior to the determining in step (a). Any suitable technique for converting intracellular folate PGS to MGs can be used, such as those disclosed in, for example, Pfeiffer Clin Chem 50(2):423-432, 2004. In a further preferred embodiment, the treating comprises (a) converting intracellular folate PGs to MGs by use of plasma conjugase; and (b) deproteinizing the MGs by acid treatment.

Exemplary conditions for converting folate PGs to MGs can be found, for example, in Pfeiffer Clin Chem 50(2):423-432, 2004. Exemplary conditions for deproteinizing MGs can be found, for example, in US 20100159493 (teaching deproteinization of MTX MGs), incorporated herein by reference in its entirety.

In one non-limiting embodiment, the biological sample comprises erythrocytes and folate PGs are converted to MGs by adding plasma containing a reducing agent in an acid pH (for example, ascorbic acid or perchloric acid) and then performing the deproteinization.

In a preferred embodiment, the treating comprises conversion of 5,10CH2THF and 10CHOTHF to 5,10methenyltetrahydrofolate (5,10CH=THF), to simplify the resulting analysis. In this embodiment, it is further preferred that determining the intracellular amount of the non-methylated folate PGs comprises separation and detection of 5,10CH=THF and 10CHOTHF, using any suitable technique, such as those discussed above (ie, reverse phase high performance liquid chromatography combined with tandem mass spectrometric detection (LC MS/MS), a microbiological assay, a dipstick assay, and liquid chromatography coupled with fluorometric detection).

As used herein, "assessing efficacy of the MTX dosing regimen in the patient" based on the amount of 5CH3THF PGs and non-methylated folate PGs, can include any suitable assessment, including an assessing MTX treatment efficacy in the patient, determining an appropriate MTX dosing regimen in the patient, assessing a risk of toxicity to MTX therapy in the patient, assessing a propensity for the patient to retain/rapidly excrete MTX, and assessing patient compliance with a prescribed MTX dosing regimen. In one preferred embodiment, an intracellular 5CH3THF PG level outside a range of between about 100 nmol/L and about 400 nmol/L (more preferably between about 125 nmol/L and about 350 nmol/L, and even more preferably between about 150 nmol/L and about 300 nmol/L) indicates that the MTX dosage should be adjusted, preferably increased to decrease methylated folates, but with the increase minimized to limit the increase in the non-methylated folate PGS that decrease MTX efficacy. In another preferred embodiment, an intracellular non-methylated folate PG level above about 50 nmol/L (preferably above about 75 nmol/L, 100 nmol/L, 125 nmol/L or 150 nmol/L) indicates that the MTX dosage should be decreased. In a still further embodiment, an intracellular non-methylated folate PG percentage of total folate PG above 40% indicates a need to decrease MTX dosage in the patient.

In one preferred embodiment, an intracellular 5CH3THF PG level below about 50 nmol/L (preferably below about 45 nmol/L, about 40 nmol/L, about 35 nmol/L, about 30 nmol/L, or about 25 nmol/L) indicates a likelihood of toxicity in the patient, and thus indicates a need to decrease the MTX dosage and/or switching to another therapeutic.

In a third aspect, the present invention provides non-transitory computer readable storage media, for automatically carrying out the methods of the invention, or certain steps thereof (ex: determining, comparing, and/or assessing steps), on a detection device, such as those disclosed herein (ex: reverse phase high performance liquid chromatography combined with tandem mass spectrometric device (LC MS/MS), a microbiological assay, a device for carrying out liquid chromatography coupled with fluorometric detection, an ELISA device, a mass spectrometry device, etc.). As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

EXAMPLE 1

Referring now to the invention in more detail, in FIG. 1 there is shown a non-limiting example of the method where the propensity for a given patient with autoimmune disease to appropriately retain MTX is indirectly measured by detecting DHFR levels using standard enzyme immunosorbent assays (ELISA) or by flow cytometry. In the present method the detection of MTX and MTXPGs is conducted indirectly by measuring DHFR levels using standard ELISA and FACS assays in various cell tissues including but not limited to whole blood, isolated erythrocytes, isolated reticulocytes, isolated peripheral mononuclear cells, CD4+ cells, CD8+ cells, monocytes, neutrophils, platelets and other immune cells. Anticoagulated blood from a patient about to start MTX is collected and predose DHFR levels are measured using ELISA or flow cytometry (expressed as Unit or activity per number of cell or volume of blood). These predose levels are expected to be very low or undetectable in circulating blood prior to MTX therapy. Immediately after blood draw the patient is instructed to take a single dose test of MTX. About 6-8 days after taking MTX a second blood draw is collected and post dose DHFR levels (apex levels) are determined. The induction level corresponding to the difference between the pre- and post-dose DHFR level is calculated and compared to a standard range established in a population of patients receiving similar MTX dosages for the indicated period (e.g. 6-8 days after starting therapy). Individuals presenting with low DHFR levels indicate low polyglutamation and retention of MTX. These patients may be underdosed and require intervention consisting of a switch from oral to parenteral MTX or an increase in MTX dose. Alternatively, DHFR levels within the 5th percentile indicate that the patient is a likely rapid excretor. The fold induction in DHFR or the absolute level changes from baseline after one single dose MTX not only indicate whether MTX has been retained in intracellularly but also indicate quantitatively the extend of the bioactivation of the drug. Thus DHFR levels generally serves as a marker of MTX exposure and more specifically as a marker of early exposure at a time where MTXPGs are usually not detected in circulation. Moreover, the pharmacokinetics of MTX and MTXPG accumulation in erythrocytes and peripheral mononuclear cells will follow a pattern in which DHFR levels will rise as function of MTX concentrations. This method can also use to monitor compliance to treatment as the return of DHFR levels to predose levels indicate the absence of MTX in cells.

EXAMPLE 2

Figure 2:
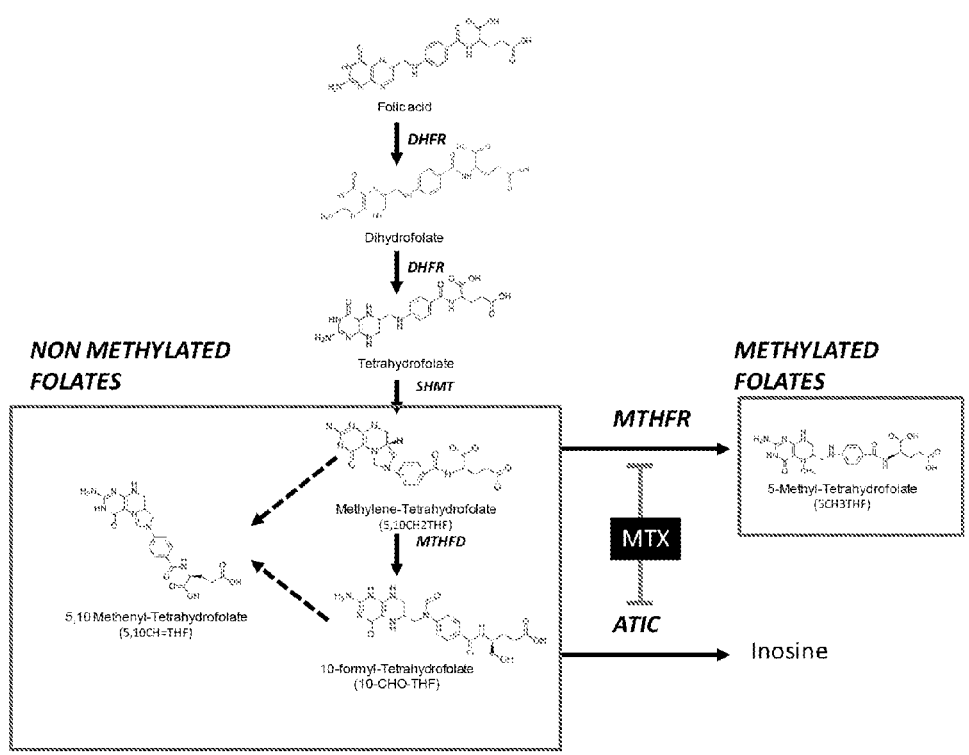
FIG. 2 shows of folate metabolism, including non-methylated and methylated folates.

FIGS. 2 and 3 describe the metabolism of folates and non-limiting examples of the changes in methylated and non-methylated folate polyglutamate concentrations following MTX concentrations. Non methylated folate polyglutamate levels correspond to 5,10 methylenetetrahydrofolate (5,10CH2THF) and 10-formyltetrahydrofolate polyglutamates (10CHOTHF). Methylated folate polyglutamate levels correspond to 5-methyltetrahydrofolate (5CH3THF). In this method whole blood is drawn in vacutainers from a patient about to start MTX or receiving MTX. Alternatively capillary blood is collected by lancet from the finger on absorbent filter paper, allowed to saturate the paper and is air dried for several hours. Following blood collection, intracellular folate polyglutamate species are converted to monoglutamate by plasma conjugase and deproteinized using acid. During the sample treatment procedure in acidic conditions 5,10CH2THF and 10CHOTHF are converted to 5,10methenyltetrahydrofolate (5,10CH=THF). The analytical separation and detection of 5,10CH=THF (non methylated folate) and 5CH3THF (methylated folate) is conducted on reverse phase high performance liquid chromatographic methods coupled with tandem mass spectrometric detection (LC MS/MS) (Garratt et al., 2005; Smulders et al., 2007; Fazili et al., 2008). Dihydrofolate are also detected by LC/MS/MS.

In FIG. 3 some examples of the changes in methylated and non methlylated folate during the course of MTX therapy are illustrated. Low dose MTX produces inhibition of MTHFR which specifically lowers 5-methyltetrahydrofolate concentrations to produces anti-inflammatory effects. In the early phase of treatment this effect is mediated by dihydrofolate polyglutamates. The decrease in methylated folate concentration is also balanced with a concurrent increase in non methylated folates that counteract MTX's effects on AICAR transformylase. In this method MTX dosing is adjusted to achieve methylated folate polyglutamate concentration ranging from 150 to 300 nmol/L (whole blood). Levels above 300 nmol/L are associated with lack of efficacy while levels below 150 nmol/L tend to be associated with increased risk for idiosyncratic reactions. The progressive increase in non methylated folate polyglutamate alleviates the inhibitory effects of MTX on de novo purine biosynthesis, and thus is antagonistic. More specifically non methylated folate above 150 nmol/L (whole blood) are associated with decreased MTX efficacy, and their emergence above that level reveal a phenotype characterized by resistance upon further dosage escalation.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Reference List

Allegra C J, Drake J C, Jolivet J and Chabner B A (1985) Inhibition of Phosphoribosylaminoimidazolecarboxamide Transformylase by Methotrexate and Dihydrofolic Acid Polyglutamates. *Proc Natl Acad Sci USA* 82:4881-4885.

Allegra C J, Fine R L, Drake J C and Chabner B A (1986) The Effect of Methotrexate on Intracellular Folate Pools in Human MCF-7 Breast Cancer Cells. Evidence for Direct Inhibition of Purine Synthesis. *J Biol Chem* 261:6478-6485.

Allegra C J, Hoang K, Yeh G C, Drake J C and Baram J (1987) Evidence for Direct Inhibition of De Novo Purine Synthesis in Human MCF-7 Breast Cells As a Principal Mode of Metabolic Inhibition by Methotrexate. *J Biol Chem* 262: 13520-13526.

Angelis-Stoforidis P, Vajda F J and Christophidis N (1999) Methotrexate Polyglutamate Levels in Circulating Erythrocytes and Polymorphs Correlate With Clinical Efficacy in Rheumatoid Arthritis. *Clin Exp Rheumatol JID*-8308521 17:313-320.

Bagley P J and Selhub J (1998) A Common Mutation in the Methylenetetrahydrofolate Reductase Gene Is Associated With an Accumulation of Formylated Tetrahydrofolates in Red Blood Cells. *Proceedings of the National Academy of Sciences of the United States of America* 95:13217-13220.

Chabner B A, Allegra C J, Curt G A, Clendeninn N J, Baram J, Koizumi S, Drake J C and Jolivet J (1985) Polyglutamation of Methotrexate. Is Methotrexate a Prodrug? *J Clin Invest* 76:907-912.

Chladek J, Martinkova J, Simkova M, Vaneckova J, Koudelkova V and Nozickova M (1998) Pharmacokinetics of Low Doses of Methotrexate in Patients With Psoriasis Over the Early Period of Treatment. *Eur J Clin Pharmacol* 53:437-444.

Cronstein B N (2005) Low-Dose Methotrexate: a Mainstay in the Treatment of Rheumatoid Arthritis. *Pharmacol Rev* 57:163-172.

Cronstein B N, Naime D and Ostad E (1993) The Antiinflammatory Mechanism of Methotrexate. Increased Adenosine Release at Inflamed Sites Diminishes Leukocyte Accumulation in an in Vivo Model of Inflammation. *J Clin Invest JID*-7802877 92:2675-2682.

Dalrymple J M, Stamp L K, O'Donnell J L, Chapman P T, Zhang M and Barclay M L (2008) Pharmacokinetics of Oral Methotrexate in Patients With Rheumatoid Arthritis. *Arthritis Rheum* 58:3299-3308.

Dervieux T, Zablocki R, and Kremer, Joel M. The Sequential Addition of Glutamic Residues On Methotrexate Selectively Potentiates the Efficacy of This Prodrug in Rheumatoid Arthritis [abstract]. Arthritis Rheum 59, 5399. 2009b.
Ref Type: Abstract Dervieux T, Zablocki R and Kremer J M (2009a) Preliminary Estimates and Significance of Red Blood Cell Methotrexate Polyglutamate Measurements In the Rheumatology Practice Setting. Arthritis and Rheumatism 60: Abstract 1619.

Dervieux T, Furst D, Lein D O, Capps R, Smith K, Caldwell J and Kremer J (2005) Pharmacogenetic and Metabolite Measurements Are Associated With Clinical Status in Patients With Rheumatoid Arthritis Treated With Methotrexate: Results of a Multicentred Cross Sectional Observational Study. *Ann Rheum Dis* 64:1180-1185.

Dervieux T, Furst D, Lein D O, Capps R, Smith K, Walsh M and Kremer J (2004) Polyglutamation of Methotrexate With Common Polymorphisms in Reduced Folate Carrier, Aminoimidazole Carboxamide Ribonucleotide Transformylase, and Thymidylate Synthase Are Associated With Methotrexate Effects in Rheumatoid Arthritis. *Arthritis Rheum JID*-0370605 50:2766-2774.

Dervieux T, Greenstein N and Kremer J (2006) Pharmacogenomic and Metabolic Biomarkers in the Folate Pathway and Their Association With Methotrexate Effects During Dosage Escalation in Rheumatoid Arthritis. *Arthritis Rheum* 54:3095-3103.

Ercikan-Abali E A, Banerjee D, Waltham M C, Skacel N, Scotto K W and Bertino J R (1997) Dihydrofolate Reductase Protein Inhibits Its Own Translation by Binding to Dihydrofolate Reductase MRNA Sequences Within the Coding RegionGÇá. *Biochemistry* 36:12317-12322.

Fazili Z, Pfeiffer C M, Zhang M, Jain R B and Koontz D (2008) Influence of 5,10-Methylenetetrahydrofolate Reductase Polymorphism on Whole-Blood Folate Concentrations Measured by LC-MS/MS, Microbiologic Assay, and Bio-Rad Radioassay. *Clinical Chemistry* 54:197-201.

Garratt L C, Ortori C A, Tucker G A, Sablitzky F, Bennett M J and Barrett D A (2005) Comprehensive Metabolic Profiling of Mono- and Polyglutamated Folates and Their Precursors in Plant and Animal Tissue Using Liquid Chromatography/Negative Ion Electrospray Ionisation Tandem Mass Spectrometry. *Rapid Commun Mass Spectrom* 19:2390-2398.

Hornung N, Ellingsen T, Attermann J, Stengaard-Pedersen K and Poulsen J H (2008) Patients With Rheumatoid Arthritis Treated With Methotrexate (MTX): Concentrations of Steady-State Erythrocyte MTX Correlate to Plasma Concentrations and Clinical Efficacy. *J Rheumatol* 35:1709-1715.

Kremer J M and Lee J K (1986) The Safety and Efficacy of the Use of Methotrexate in Long-Term Therapy for Rheumatoid Arthritis. *Arthritis Rheum JID*-0370605 29:822-831.

Matthews R G and Daubner S C (1982) Modulation of Methylenetetrahydrofolate Reductase Activity by S-Adenosylmethionine and by Dihydrofolate and Its Polyglutamate Analogues. *Adv Enzyme Regul* 20:123-131.

Smulders Y M, Smith D E, Kok R M, Teerlink T, Gellekink H, Vaes W H, Stehouwer C D and Jakobs C (2007) Red Blood Cell Folate Vitamer Distribution in Healthy Subjects Is Determined by the Methylenetetrahydrofolate Reductase C677T Polymorphism and by the Total Folate Status. *J Nutr Biochem* 18:693-699.

Stamp L K, Chapman P T, O'Donnell J L, Zhang M, James J, Frampton C, Barclay M L, Kennedy M A and Roberts R L (2010a) Polymorphisms Within the Folate Pathway Predict Folate Concentrations but Are Not Associated With Disease Activity in Rheumatoid Arthritis Patients on Methotrexate. *Pharmacogenet Genomics* 20:367-376.

Stamp L K, O'Donnell J L, Chapman P T, Zhang M, James J, Frampton C and Barclay M L (2010b) Methotrexate Polyglutamate Concentrations Are Not Associated With Disease Control in Rheumatoid Arthritis Patients Receiving Long-Term Methotrexate Therapy. *Arthritis Rheum* 62:359-368.

I claim:

1. A method for assessing efficacy of a methotrexate (MTX) dosing regimen in a patient, comprising
   (a) determining an intracellular amount of
      (i) 5-methyltetrahydrofolate (5CH3THF) polyglutamates (PGs); and
      (ii) non-methylated folate PGs
   in a biological sample from the patient before or after initiation of MTX treatment or modification of MTX treatment in the patient; and
   (b) assessing efficacy of the MTX dosing regimen in the patient based on the amount of 5CH3THF PGs and the amount of non-methylated folate PGs.

2. The method of claim 1, wherein assessing the efficacy of the MTX dosing regimen comprises one or more of (a) assessing MTX treatment efficacy in the patient; (b) determining an appropriate MTX dosing regimen in the patient; and (c) assessing a propensity for the patient to retain MTX.

3. The method of claim 1, wherein determining the intracellular amount of 5CH3THF PGs and non-methylated folate PGs is carried out after initiation or after modification of MTX treatment in the patient.

4. The method of claim 1, wherein the biological sample is treated to convert intracellular folate PGs in the biological sample to monoglutamates (MGs) prior to the determining in step (a).

5. The method of claim 4, wherein the treating comprises
   (a) converting intracellular folate PGs to MGs by use of plasma conjugase; and
   (b) deproteinizing the MGs by acid treatment.

6. The method of claim 1, wherein the non-methylated PGs are selected from the group consisting of tetrahydrofolate (THF) PGs; 5 methylenetetrahydrofolate (5MeTHF) PGs; 5,10 methylenetetrahydrofolate (5,10CH2THF) PGs; dihydrofolate polyglutamates, and 10-formyltetrahydrofolate (10CHOTHF) PGs.

7. The method of claim 1, wherein the non-methylated PGs are 5,10 methylenetetrahydrofolate (5,10CH2THF) PGs and 10-formyltetrahydrofolate (10CHOTHF) PGs.

8. The method of claim 7, wherein the biological sample is treated to convert intracellular folate PGs in the biological sample to monoglutamates (MGs) prior to the determining in step (a), and wherein the treating comprises conversion of 5,10CH2THF and 10CHOTHF to 5,10methenyltetrahydrofolate (5,10CH=THF).

9. The method of claim 8, wherein the determining the intracellular amount of the non-methylated folate PGs comprises separation and detection of 5,10CH=THF and 10CHOTHF.

10. The method of claim 1, wherein determining the intracellular amount of 5CH3THF PGs and non-methylated folate PGs comprises a method selected from the group consisting of reverse phase high performance liquid chromatography combined with tandem mass spectrometric detection (LC MS/MS), a microbiological assay, a dipstick assay, and liquid chromatography coupled with fluorometric detection.

11. The method of claim 1, wherein an intracellular 5CH3THF PG level outside a range of between about 100 nmol/L and about 400 nmol/L indicates that the MTX dosage should be adjusted.

12. The method of claims 1, wherein an intracellular non-methylated folate PG level above about 50 nmol/L indicates that the MTX dosage should be decreased.

13. The method of claim 1, wherein an intracellular non-methylated folate PG percentage of total folate PG above 40% indicates a need to decrease MTX dosage in the patient.

14. The method of claim 1, wherein an intracellular 5CH3THF PG level below about 50 nmol/L indicates a likelihood of toxicity in the patient.

15. The method of claim 1, wherein the patient suffers from an inflammatory disease or cancer.

16. The method of claim 15, wherein the patient suffers from an autoimmune disorder.

17. The method of claim 1, wherein the biological sample is selected from the group consisting of whole blood, erythrocytes, reticulocytes, leukocytes, peripheral mononuclear cells, CD4+ cells, CD8+ cells, monocytes, neutrophils, and platelets.

18. The method of claim 1, wherein assessing the efficacy of the MTX dosing regimen comprises determining an appropriate MTX dosing regimen in the patient.

19. The method of claim 1, wherein assessing the efficacy of the MTX dosing regimen comprises assessing a propensity for the patient to retain MTX.

20. The method of claim 1, wherein determining the intracellular amount of 5CH3THF PGs and non-methylated folate PGs is carried out after modification of MTX treatment in the patient.

21. The method of claim 16, wherein the autoimmune disorder is selected from the group consisting of rheumatoid arthritis, Crohn's disease, ulcerative colitis, and systemic lupus erythematosus.

22. The method of claim 1, wherein the biological sample comprises whole blood, leukocytes, and/or erythrocytes.

* * * * *